United States Patent [19]

Grassme et al.

[11] Patent Number: 4,618,974
[45] Date of Patent: Oct. 21, 1986

[54] DENTAL X-RAY DIAGNOSTIC UNIT

[75] Inventors: Ulrich Grassme, Nuremberg; Erich Noske, Weiher, both of Fed. Rep. of Germany

[73] Assignee: Siemens Aktiengesellschaft, Berlin and Munich, Fed. Rep. of Germany

[21] Appl. No.: 576,583

[22] Filed: Feb. 3, 1984

[30] Foreign Application Priority Data

Feb. 8, 1983 [DE] Fed. Rep. of Germany ....... 3304271

[51] Int. Cl.$^4$ ........................................... G03B 41/16
[52] U.S. Cl. ...................................... 378/40; 378/110; 378/116; 378/112
[58] Field of Search .................... 378/38, 39, 40, 116, 378/112, 110, 108

[56] References Cited

U.S. PATENT DOCUMENTS 4,160,906 7/1979 Daniels ............................... 378/116
4,501,010 2/1985 Grassme ............................. 378/38

Primary Examiner—Craig E. Church
Attorney, Agent, or Firm—Mark H. Jay

[57] ABSTRACT

The invention concerns a dental X-ray diagnostic unit for panoramic planigraphy, with a radiation source, an X-ray film cassette that is moved during the exposure in relation to the radiation source, with an adjusting mechanism to move the radiation source and the cassette around the object, and with a slit stop located in the radiation path between the radiation source and the cassette. For a given exposure process, the time sequence of the dosage from the radiation source can be predetermined by a control apparatus.

2 Claims, 1 Drawing Figure

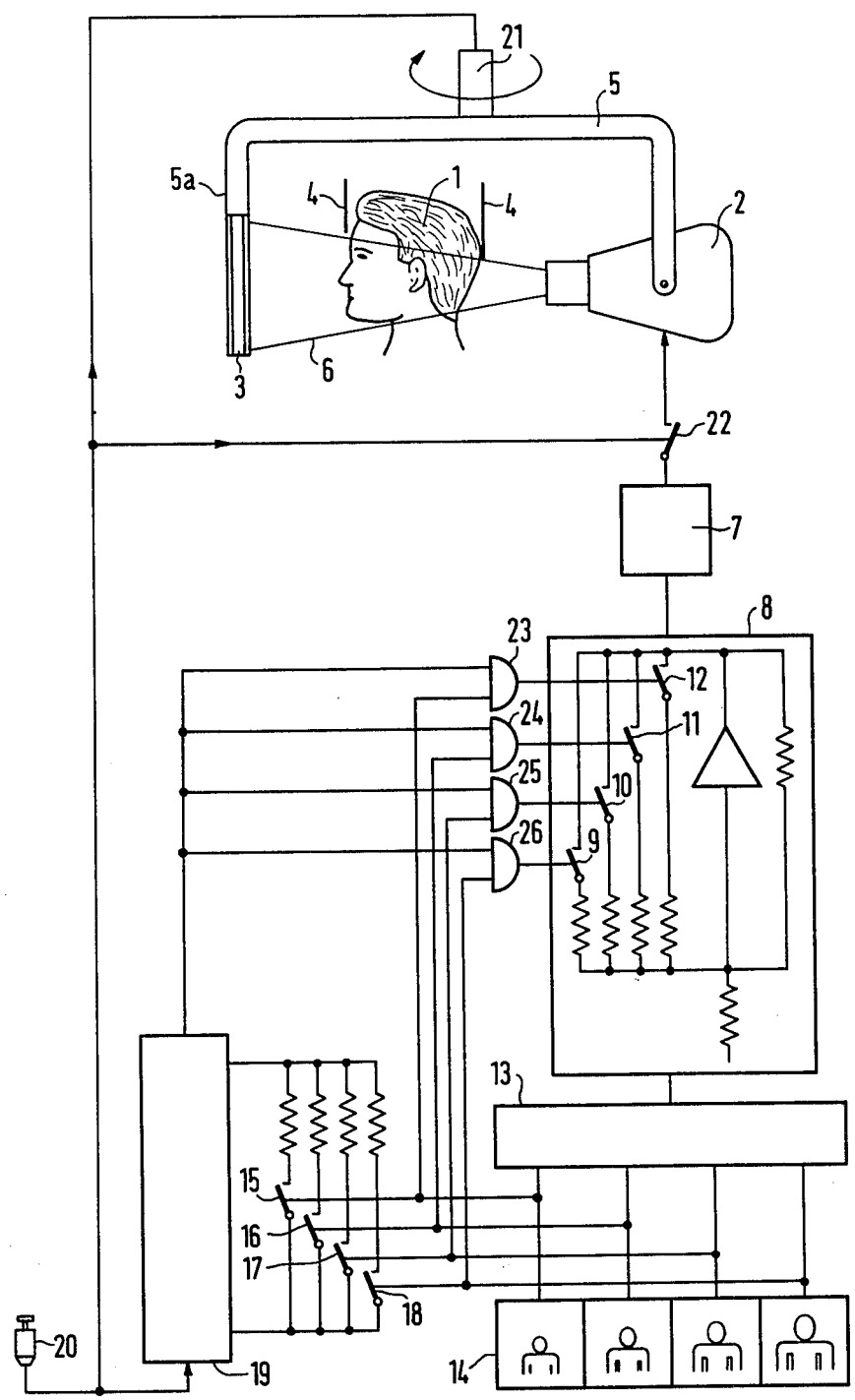

DENTAL X-RAY DIAGNOSTIC UNIT

BACKGROUND OF THE INVENTION

This invention is related to a dental X-ray diagnostic unit used to produce panoramic planigraphs of an object, with a radiation source, a cassette that exposes the X-ray film and moves during the exposure with respect to the radiation source, with an adjusting device that is used to move the radiation source and the cassette around the object, and with a slit stop located in the radiation path between the radiation source and the cassette to limit the radiation beam.

A dental X-ray diagnostic unit of this type is described in German patent application P 24 47 075.5. By means of this X-ray diagnostic unit, panoramic planigraphs of the jaw can be produced. For this purpose the patient's cranium is held steady in a head support. The X-ray tube and the cassette with the X-ray film are moved around the patient in such a way that an image of the entire jaw can be obtained on the film in a single exposure. The picture taken in this manner is a planigraph, in which a desired image quality required for a diagnosis is present only within a certain layer. The zones lying outside this clear layer appear as blurred images. With this process, the thickness of the clearly imaged layer is proportional to the respective radius of curvature of the layer and inversely proportional to the width of the radiation beam and accordingly also to the width of the slit stop that determines the width of the radiation beam.

In an X-ray diagnostic unit of this kind, it is desirable to increase the dosage from the radiation source during the exposure in the course of traversing specific areas, in particular the area of the spinal column.

The invention is designed to perform the function of producing a dental diagnostic unit of the type described above, in which the dosage can be optimally adjusted to the individual patient.

SUMMARY OF THE INVENTION

According to the invention, this task is achieved by providing controls to regulate the dosage during the exposure process. In connection therewith, program switching devices for the selection of control programs are provided. In the X-ray diagnostic unit according to the invention, optimal sequences for the dosage during the exposure process can be stored by means of a number of control programs. The program that is most suitable in each case can be selected by the program switching devices in accordance with the patient's condition and constitution. When this process is used, it is possible to predetermine the dosage during the course of the exposure by the control program selected for the specific case both with regard to the dosage and with regard to the length of time that it lasts.

Other features and advantages of the invention will be apparent from the following description of the preferred embodiments, and from the claims.

For a full understanding of the present invention, reference should now be made to the following detailed description of the preferred embodiments of the invention and to the accompanying drawings.

BRIEF DESCRIPTION OF THE DRAWINGS

FIG. 1 of the drawing is a diagrammatic view of a preferred embodiment of the invention.

DETAILED DESCRIPTION

The invention is described in greater detail below with reference to FIG. 1 of the drawings.

The single FIGURE shows a dental X-ray diagnostic unit used to produce panoramic planigraphs of a patient 1 with a radiation source 2 and a cassette 3 that exposes an X-ray film. The head of the patient 1 is held in place by a support 4 during an exposure process, during which the X-ray tube 2 and the cassette 3 are moved around him. Both the cassette 3 and the X-ray tube 2 are mounted on a carrier 5, which moves these components during the course of the exposure in the direction shown by the arrow. The focusing of the X-ray beam 6 is accomplished in a familiar manner by means of a slit stop located in the X-ray tube housing and a secondary slit stop located close to the film on the arm part 5a of the carrier 5. Through these means the X-ray beam 6 is focused in the form of a line in the vertical direction.

The X-ray tube 2 is fed by a generator 7 to which an amplifier 8 is connected to provide the specific dosage in each case. In order to provide the basic value of a respective dosage, the amplification produced by the amplifier 8 can be controlled by a setting device 13 to which object pushbuttons 14 are connected. In addition to controlling the amplifier 8 through the setting device 13, the object pushbuttons 14 also control a timer 19 through contacts 15, 16, 17 and 18

When the trigger 20 is pressed, a motor 21 is turned on, which causes the X-ray tube 2 and the film cassette 3 to move around the patient 1. In addition, a contact 22 is closed, which turns on the X-ray tube 2. At the end of the predetermined exposure time, X-ray tube 2 and cassette 3 come to their respective rest position again and contact 22 is opened.

For the optimal predetermination of the dosage sequence a selected one of the pushbuttons 14 is pressed, according to the constitution of the patient being examined. This causes, in the first place, an initial value for the dosage emitted by the X-ray tube 2 to be given through the setting device 13. In addition, however, as a result of the closing of one of the contacts 15 to 18, a time period for the dosage is predetermined, that is, a period within the course of the exposure process, during which the dosage is increased. As a result it is raised to a value which is likewise predetermined through contacts 9 to 12 in accordance with the setting of the pushbuttons 14.

After exposure trigger 20 has been activated, the exposure begins, with the dosage corresponding to one of the pushbuttons 14 that has been pressed. At the end of the time period predetermined by one of the contacts 15 to 18 which has been closed, the timer 19 sends a signal to the AND-circuits 23 to 26. The second input signal for the activated AND-circuit comes from the pushbutton 14 that has been pressed. At that point, the dosage is accordingly raised to a value predetermined by the pushbutton 14.

In summary, it is clear that by means of the pushbuttons 14, it is possible to predetermine, on the one hand, the initial value of the dosage and the higher values that occur in the course of the exposure, and, on the other hand, the time during which the higher value for the dosage is maintained, for a given exposure process on the basis of the patient's constitution.

There has thus been shown and described novel apparatus for dental X-ray which fulfills all the objects and advantages sought therefor. Many changes, modifications, variations and other uses and applications of the subject invention will, however, become apparent to those skilled in the art after considering this specification and the accompanying drawings which disclose preferred embodiments thereof. All such changes, modifications, variations and other uses and application which do not depart from the spirit and scope of the invention are deemed to be covered by the invention which is limited only by the claims which follow.

What is claimed is:

1. An improved dental X-ray diagnostic unit for producing panoramic planigraphs of an object of a type having:
    (a) a radiation source;
    (b) a cassette for holding an X-ray film substantially diametrically opposite said radiation source;
    (c) an adjusting mechanism for moving said radiation source and said cassette around said object; and
    (d) a slit stop located in the radiation path between said radiation source and said cassette for limiting a radiation beam generated by said radiation source, wherein the improvement comprises switching devices for varying intensity of the X-ray beam during the exposure of said object to said radiation beam, said switching devices further including pushbutton switching devices for selecting a desired X-ray dosage.

2. The improvement of claim 1, wherein said pushbutton switching devices select programs which vary beam intensity in a predetermined manner.